United States Patent [19]

Waites et al.

[11] 4,225,590

[45] Sep. 30, 1980

[54] MALE FERTILITY-INHIBITING COMPOSITIONS OF 6-CHLORODEOXY-SACCHARIDES

[75] Inventors: Geoffrey M. H. Waites; William C. L. Ford; Riaz A. Khan; Haydn F. Jones, all of Berkshire, England

[73] Assignee: Tate & Lyle Limited, London, England

[21] Appl. No.: 886,531

[22] Filed: Mar. 14, 1978

[30] Foreign Application Priority Data

Mar. 14, 1977 [GB] United Kingdom ............... 10694/77

[51] Int. Cl.³ .......................... A61K 31/70; C07H 5/02
[52] U.S. Cl. ......................................... 424/180; 536/1; 536/122
[58] Field of Search ...................... 536/1, 122; 424/180

[56] References Cited

U.S. PATENT DOCUMENTS

2,684,961    8/1954    Barham ................................. 536/122

FOREIGN PATENT DOCUMENTS

2700917    7/1977    Fed. Rep. of Germany ........... 536/122

OTHER PUBLICATIONS

Khan et al., Carbohydrate Research 39 (1975), 253–262.
Evan and Parrish, *Methods in Carbohydrate Chemistry*, vol. VI (1972), p. 193.
Brauns, J. Amer. Chem. Soc. 42, (1920), 1850.
Wood et al., J. Chem. Soc.(c), 1966, pp. 1994–1997.
Ford, W., and Waites, G., J. Reprod. Fert. (1978), 52, 153–157.
Ford, W., et al., J. Reprod. Fert. (1977) 51, 105–109.
Chem. Abstract Citation, vol. 83 (59219v) 1975.

*Primary Examiner*—Johnnie R. Brown
*Assistant Examiner*—Blondel Hazel
*Attorney, Agent, or Firm*—Ostrolenk, Faber, Gerb & Soffen

[57] ABSTRACT

A male fertility-inhibiting composition in unit dosage form, contains as an active ingredient a 6-chlorodeoxy-saccharide containing a pyranose or furanose ring of the formula where A represents the remainder of the pyranose or furanose ring, and has the formula $C_4H_7O_4X$ (where X represents a hydrogen atom or another pyranose or furanose ring) in association with a physiologically acceptable carrier or excipient. The saccharide preferably contains a pyranose ring or furanose ring of the formula Also a method of controlling fertility in men or male animals comprises administering thereto a 6-chlorodeoxy-saccharide as defined above.

11 Claims, No Drawings

MALE FERTILITY-INHIBITING COMPOSITIONS OF 6-CHLORODEOXY-SACCHARIDES

This invention relates to chemical compositions possessing male fertility-inhibiting action.

At present, the only systematic method of fertility control available involves the administration of hormones or hormone-like substances to the female, generally to interfere with the normal menstrual or oestrous cycle. Considerable research has been undertaken to find an equivalent systematic method of fertility control in the male, so far without any real success. This research has generally been concerned with hormone-type action, although more recently attention has turned to the use of chemical substances having no hormonal affect, but instead possessing an entirely local action on the sperm.

One particular field of activity which is of considerable interest is intervention in the process of sperm maturation in the epididymis. This is an attractive approach to fertility regulation in the male since methods having this mechanism of action would not depress spermatogenesis or libido. Maturation of the sperm in the epididymis requires several days and the passage of the mature sperm through the epididymis lasts seven to twelve days, during which time the motility of the sperm is promoted. Thus, interference with this process can, in theory, produce immotile sperm which are hence non-fertile.

One substance which has previously been of considerable interest is racemic α-chlorohydrin. However, this compound has recently been reported to have undesirable side effects and hence interest in racemic α-chlorohydrin has waned.

We have now discovered that certain 6-chlorodeoxysaccharides, when administered orally to the male, have the ability to render the subject infertile. While we do not wish to be bound by theory, we believe this action is due to a depression of the sperm motility. Fertility is subsequently fully regained on cessation of the treatment.

According to the present invention, therefore, we provide a male fertility-inhibiting composition in unit dosage form, containing as an active ingredient a 6-chlorodeoxy monosaccharide or 6-chlorodeoxy disaccharide containing a pyranose or furanose ring of the formula

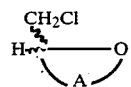

where A represents the remainder of the pyranose or furanose ring, and has the formula $C_4H_7O_4X$ (where X represents a hydrogen atom or another pyranose or furanose ring) in association with a physiologically acceptable carrier or excipient. The saccharide may, in particular, contain a pyranose ring of the formula

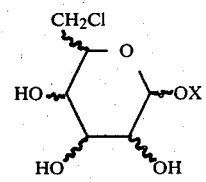

where X represents a hydrogen atom or a pyranose or furanose ring, for example, 6-chloro-6-deoxy-glucose; 6-chloro-6-deoxy-sucrose; 6,6'-dichloro-6,6'-di-deoxy-sucrose; 6-chloro-6-deoxy-galactose; and 6-chloro-6-deoxy-mannose.

The saccharide may alternatively contain a furanose ring of the formula

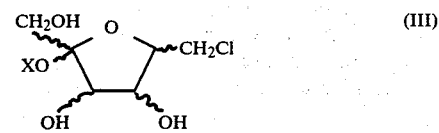

where X represents a hydrogen atom or a pyranose or furanose ring, for example, 6-chloro-6-deoxy-fructose and 6'-chloro-6'-deoxy-sucrose.

It will be understood, however, that saccharides may, in solution, undergo mutarotation to give an equilibrium mixture of pyranose and furanose forms. The same is true of the 6-chloro derivatives of the present invention and although the compounds are represented in one form, the invention is to be understood to include the alternative form or forms and also mixtures of such forms.

The invention also provides a method of controlling the fertility of male animals, which term is taken to include fertility control in humans and also in the veterinary field, by administering thereto a 6-chlorodeoxy-monosaccharide or 6-chlorodeoxy-disaccharide containing a pyranose or furanose ring of the general formula (I) as defined above, in an amount effective to control fertility.

Many of the compounds of use in compositions according to the invention are known per se, but none is reported to possess any systemic pharmacological activity. The following compounds are all known per se and are disclosed, for example, in the following literature references:

6,6'-dichloro-6,6'-di-deoxy-sucrose: British Patent Specification No. 1 430 288; 6'-chloro-6'-deoxy-sucrose: Khan, Jenner, and Mufti, Carbohydrate Research 39 (1975) 253–262; 6-chloro-6-deoxy-sucrose: idem., ibid.; 6-chloro-6-deoxy-D-glucose: Evans and Parrish, Methods in Carbohydrate Chemistry (Ed. R. L. Whistler and J. N. B. Miller) Vol. VI(1972) p. 193; 6-chloro-6-deoxy-fructose: Brauns. J. Amer. Chem. Soc. 42 (1920) 1850; 6-chloro-6-deoxy-galactose: Wood, Fisher and Kent J. Chem. Soc. (C), 1966 pp. 1994–1997.

6-Chloro-6-deoxy-mannose is unreported and details of its physical characteristics are given in the Examples which follow.

The compounds may be prepared by any convenient method for obtaining chloro sugars. In general, the unchlorinated sugar is reacted with an appropriate chlorinating agent, if necessary after first having been protected against unwanted chlorination at positions other than the 6-position. In particular, the anomeric centre (the reducing centre) must be protected if not already in a non-reducing structure as in, for example, sucrose. The centre may be protected, for example, by methylation or by the formation of acetal derivatives such as isopropylidene-bridged derivatives. Various suitable chlorinating agents include methanesulphonyl chloride in D.M.F., and triphenylphosphine in carbon tetrachloride.

6-Chlorodeoxy-monosaccharides can also be obtained by hydrolysis of a corresponding 6-chlorodeoxy-disaccharide. Thus, for example, 6-chloro-6-deoxy-fructose can be obtained by acid hydrolysis of 6'-chloro-6'-deoxy-sucrose.

It will be understood that pharmaceutically acceptable bioprecursors of the 6-chloro-6-deoxy-saccharides can be used in place of the 6-chloro-6-deoxy saccharides themselves, both in the compositions and in the method according to the invention. For example, acetal derivatives formed as intermediates in the preparation of the compounds will be broken down in vivo to provide the compounds in situ. A typical example is 6-chloro-6-deoxy-1,2:3,4-di-O-isopropylidene-D-galactose, which yields 6-chloro-6-deoxy-galactose on mild acid hydrolysis, e.g. in the stomach.

Compositions according to the present invention are preferably presented in a form for oral administration, such as tablets, coated tablets, capsules or soluble tablets. The presentation is conveniently adapted so that a dose of one or two units per day gives a sufficient level of protection. In general, each unit dosage may contain from 0.5 to 5 g, suitable for providing a daily dose of from 10 to 60 mg/kg.

Other forms of administration envisaged may include slow-release or depot formulations containing sufficient active ingredient per unit to suppress fertility for a sustained period.

The anti-fertility action of the compounds was demonstrated in a fertilization test using rats according to the following method.

In each test, a group of seven male CD rats (Charles River, Manston, Kent) was selected. Each rat weighed from 350 to 420 g. The rats were given oral doses of the compounds shown in the table each day for one week and for three consecutive weeks. At the end of the first week, one female rat designated A (body weight about 300 g, Charles River) was placed with each male and allowed to remain with the male for seven days. After seven days, female A was removed and female B was introduced. After a further seven days, female B was removed and female C was introduced. After seven days, female C was removed and the male rats were kept for three weeks without dosing. At the end of this three week period, female D was introduced. After a further three weeks without dosing, female E was introduced. Vaginal smears were taken from each female before she was put with the male, to confirm normal oestrous cycling, and whilst she was with the male until sperm were found. Females A,B,D and E were killed about ten days after sperm were detected in vaginal smears and implantation sites and corpora lutea were counted. In the first test on Compound 1, the females in batch C were kept for eighteen days after mating or allowed to litter.

The results for the three sucrose derivatives are given in the following Table 1. It will be understood that the seven males used in each test was different.

Table 1:

| | The effect of chlorinated sucroses on the fertility of male rats. | | | | | | | | | | | | | | | | | | | | | | | | |
|---|---|---|---|---|---|---|---|---|---|---|---|---|---|---|---|---|---|---|---|---|---|---|---|---|---|
| | Implantation Sites per Female | | | | | | | | | | | | | | | | | | | | | | | | |
| Male | Controls H$_2$O (1ml/kg) | | | | | Compound 1 120 μmole/kg/day | | | | | Compound 1 240 μmole/kg/day | | | | | Compound 2 240 μmole/kg/day | | | | | Compound 3 240 μmole/kg/day | | | | |
| No. | A | B | C | D | E | A | B | C[2] | D | E | A | B | C | D | E | A | B | C | D | E | A | B | C | D | E |
| 1 | 19 | 16 | 13 | — | — | 0 | 9 | 14 | — | — | 2 | 0 | 0 | — | — | 0 | 0 | 0 | — | — | 0 | 0 | 0 | — | — |
| 2 | 19 | 17 | 17 | — | — | 5 | 1 | 3 | — | — | 0 | 0 | 1[4] | — | — | 0 | 1 | 0 | — | — | 0 | 0 | 0 | — | — |
| 3 | 16 | 14 | 14 | — | — | 16 | 15 | 0 | — | — | 0 | 0 | 0 | — | — | 1 | 0 | 0 | — | — | 0 | 0 | 0 | — | — |
| 4 | 17 | 13 | 16 | 15 | 12 | 0 | 0 | 0 | 16 | 14 | 0 | 0 | 0 | 0 | 15 | 0 | 0 | 0 | 14 | 15 | 0 | 0 | 0 | 6 | 17 |
| 5 | 18 | 14 | 16 | 16 | 15 | 12 | 0 | —[3] | 0 | 15 | 0 | 0[5] | 0 | 16 | 15 | 0 | 0 | 0 | 13 | —[6] | — | — | — | — | — |
| 6 | 15 | 12 | 0[5] | 13 | 15 | 3 | 12 | 17 | 15 | 12 | 0 | 0 | 0 | 14 | 13 | 0 | 0 | 0 | 11 | 12 | 0 | 0 | 0 | 7 | 8 |
| 7 | 17 | 16 | 0[5] | 11 | 18 | 0 | 0 | 16 | 7 | 15 | 0 | 0 | 5[4] | 19 | 12 | 0 | 0 | 0 | 12 | 12 | 0 | 0 | 0 | 15 | 13 |
| Conception rate %[1] | 86 | 85 | 69 | 91 | 97 | 27 | 32 | — | 56 | 93 | 0.3 | 0 | 4.7 | | 95 | 0.1 | 0.1 | 0 | 89 | 97 | 0 | 0 | 0 | 63 | 81 |

Notes:
[1]Calculated from number of corpora lutea
[2]Live normal births
[3]Female with fused uterine horns - died from pregnancy toxaemia
[4]Morphologically normal embryos
[5]Swollen uterus
[6]Male died
Compound 1: 6,6'-dichloro-6,6'-dideoxy-sucrose.
Compound 2: 6-chloro-6-deoxy-sucrose.
Compound 3: 6'-chloro-6'-deoxy-sucrose.

As can be seen from Table 1, all three compounds when administered at a daily rate of 240 μmole/kg, were capable of suppressing fertility, in some cases completely. After six weeks without dosing, the fertility of the rats had returned.

A similar test was carried out on 6-chloro-6-deoxy-glucose and 6-chloro-6-deoxy-fructose, and also on sucrose as a control. The 6-chloro-6-deoxy-fructose was obtained by acid hydrolysis of 6'-chloro-6'-deoxy-sucrose, the unseparated mixture of 6-chloro-6-deoxy-fructose and glucose so formed being administered to the rats directly.

Each group of five male rats was dosed for seven days at the rate indicated and then females were introduced and the males dosed for a further seven days. Females were then killed 9-12 days after mating. The results are shown in Table 2, from which it can be seen that the two 6-chloro-monosaccharides were similar in activity to the 6-chloro-disaccharides.

In a further similar test, 6-chloro-6-deoxy-galactose and 6-chloro-6-deoxy-mannose showed complete suppression of fertility in rats at a daily rate of 300 μmole/kg.

Other similar trials in marmosets have indicated a similar level of activity for the compounds of use according to the invention.

TABLE 2:

The effect of chlorinated sucrose, glucose and fructose on the fertility of male rats

|  |  | Male No. 1 | 2 | 3 | 4 | 5 | Average |
|---|---|---|---|---|---|---|---|
| 6'-chloro-6'-deoxysucrose | Embryos | 1 | 0[(1)] | 0 | 0 | 9 | 2 |
| 120 μmoles/kg/day | Conception rate % | 6.7 | 0 | 0 | 0 | 53 | 12 |
| 6'-chloro-6'-deoxysucrose | Embryos | 15 | 12[(2)] | 16 | 16 | 4 | 12.6(0.4) |
| 60 μmoles/kg/day | Conception rate % | 94 | 100 | 84 | 100 | 29 | 81.4 |
| 6-chloro-6-deoxyglucose | Embryos | 0 | 0 | 0 | 0 | 0 | 0 |
| 240 μmoles/kg/day | Conception rate % | 0 | 0 | 0 | 0 | 0 | 0 |
| 6-chloro-6-deoxyfructose (+glucose) | Embryos | 0 | 0 | 0 | 0 | 0 | 0 |
| 240 μmoles/kg/day | Conception rate % | 0 | 0 | 0 | 0 | 0 | 0 |
| Sucrose (control) | Embryos | 0 | 17 | 17 | 20 | 16 | 14.0 [17.5][(2)] |
| 120 μmoles/kg/day | Conception rate % | 0 | 100 | 100 | 100 | 94 | 78.8 [98.5] |

NOtes:
[(1)]Infected left horn of uterus.
[(2)]Neglecting the infertile mating with Male No. 1
Figures in brackets denote resorbing implants; conception rate is the number of implants divided by the number of corpora lutea (percent.).

The compounds possess a low toxicity. For example, the oral $LD_{50}$ of 6-chloro-6-deoxy-glucose is above 16 g/kg in the rat and the oral $LD_{50}$ of 6,6'-dichloro-6,6'-dideoxy-sucrose is above 16 g/kg in the mouse.

The following Examples illustrate the invention further:

EXAMPLE 1

6-Chloro-6-deoxy-α-D-mannopyranose
(6-chloro-6-deoxy-mannose)

A solution of methyl α-D-mannopyranoside (20 g, 0.103 moles) in dry D.M.F. (1 liter) was cooled to 0° C. and N-chlorosuccinimide (27.6 g, 0.207 moles) and triphenylphosphine (54 g, 0.206 moles) were added successively in portions. The resulting mixture was heated at 50° C. for 2 hours, cooled and partitioned between chloroform (2 liters) and water (2 liters).

The chloroform layer was washed with water and the water layer extracted with chloroform. The water layer and the water washings were combined and evaporated to dryness. The residue was acetylated by treatment with pyridine (200 ml) and acetic anhydride (100 ml). After a conventional work-up in which succinimide was removed in water washings, the syrupy material was de-acetylated by treatment with a catalytic quantity of sodium methoxide in methanol. Evaporation of the methanol to dryness yielded methyl 6-chloro-6-deoxy-α-D-mannopyranoside (15.2 g). This compound was reported by Evans, Long and Parrish, J. Org. Chem. 33 (1968) p.1074, but was obtained using a different route.

The residue was then subjected to acetolysis by treatment with glacial acetic acid (450 ml), acetic anhydride (60 ml) and concentrated sulphuric acid (22.5 ml) at 25° C. for 70 hours. The mixture was poured into ice/water (2.5 liters) and extracted with chloroform (500 ml). The extract was washed with saturated sodium hydrogen carbonate and then with water and was dried over magnesium sulphate, filtered and evaporated. Thin-layer chromatography (ethyl acetate/petroleum ether, 2:1) on silica gel indicated that the product was homogeneous. The product was confirmed by $^1$H NMR spectroscopy to be 1,2,3,4-tetra-O-acetyl-6-chloro-6-deoxy-α-D-mannopyranoside $[\alpha]_D^{22}+55.5°$ (c 1.9 chloroform); NMR: δ6.32 (1p, H-1, $J_{1,2}=2$ Hz); δ5.8–5.5 (3p, H's 2,3 and 4, multiplet); δ4.3 (1p, H-5, multiplet); δ3.75 (2p, H's 6, multiplet); δ2.05–1.8 (12p, 4×CH$_3$—).

The tetra-acetate was then de-acetylated by treatment with a catalytic amount of sodium methoxide in methanol to yield 6-chloro-6-deoxy-α-D-mannopyranose.

Analysis:
Calc. Cl, 17.85%; Found: Cl, 17.41%. $[\alpha]_D^{18}+26.5$ (c 0.4 water).

EXAMPLE 2

Tablets

6-Chloro-6-deoxy-glucose is combined in a conventional manner with conventional tableting binders and lubricants and is pressed into tablets, each containing 2.5 g of the active ingredient.

We claim:
1. A male fertility-inhibiting composition in unit dosage form, comprising a unit dosage amount of, as active ingredient, a 6-chlorodeoxy-mono-or-di-saccharide of the formula

where A represents the remainder of a ring selected from the group consisting of a pyranose ring or a furanose ring, and has the formula C$_4$H$_7$O$_3$.OX (where OX is a substituent at the anomeric center and X is selected from the group consisting of a hydrogen atom and an aglycone, said aglycone being selected from the group consisting of pyranose, furanose and the 6'-chlorodeoxy derivative thereof) in association with a physiologically acceptable carrier or excipient.

2. The composition of claim 1, in which the saccharide is of the formula.

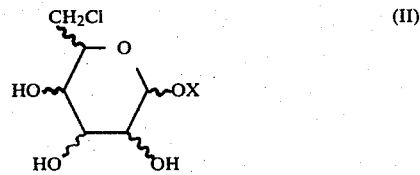

3. The composition of claim 1, in which the saccharide is selected from the group consisting of 6-chloro-6- deoxy-glucose, 6-chloro-6-deoxy-sucrose, 6,6'-dichloro-6,6'-dideoxy-sucrose, 6-chloro-6-deoxy-galactose and 6-chloro-6-deoxy-mannose.

4. The composition of claim 1, in which the saccharide is of the formula.

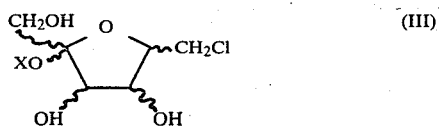

5. The composition of claim 1, in which the saccharide is selected from the group consisting of 6-chloro-6-deoxy-fructose and 6'-chloro-6'-deoxy-sucrose.

6. The composition of claim 1, wherein said unit dosage contains from 0.5 to 5 g of the said active ingredient.

7. A method of controlling fertility in men or male animals, in which a 6-chlorodeoxymono-or-di-saccharide of the formula

where A represents the remainder of a ring selected from the group consisting of a pyranose ring and a furanose ring, and has the formula $C_4H_7O_3.OX$ (where OX is a substituent at the anomeric center and X is selected from the group consisting of a hydrogen atom and an aglycone, said aglycone being selected from the group consisting of pyranose, furanose and the 6'-chlorodeoxy derivative thereof, is administered thereto in an amount effective to control fertility.

8. 6-Chloro-6-deoxy-mannose.

9. The method of claim 7 wherein said saccharide is of the formula

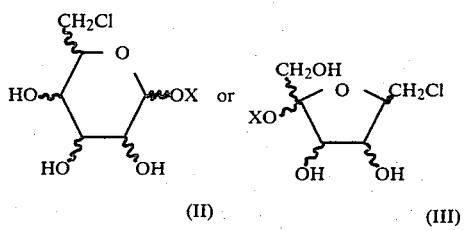

10. The method of claim 9 wherein said saccharide is selected from the group consisting of 6-chloro-6-deoxy-glucose, 6-chloro-6-deoxy-sucrose, 6,6'-dichloro-6,6'-dideoxy-sucrose, 6-chloro-6-deoxy-galactose, 6-chloro-6-deoxy-fructose, 6'-chloro-6'-deoxy-sucrose and 6-chloro-6-deoxy-mannose.

11. The method of claim 7 wherein said saccharide is administered to a male animal.

* * * * *

Disclaimer 4,225,590.—*Geoffrey M. H. Waites; William C. L. Ford; Riaz A. Khan;* and *Haydn F. Jones,* Berkshire, England. MALE FERTILITY-INHIBITING COMPOSITIONS OF 6-CHLORODEOXY-SACCHARIDES. Patent dated Sept. 30, 1980. Disclaimer filed Nov. 19, 1981, by the assignee, *Tate & Lyle, Ltd.*

Hereby enters this disclaimer to claim 8 of said patent.

[*Official Gazette September 27, 1983.*]